United States Patent
Bulinski et al.

(10) Patent No.: US 11,452,238 B2
(45) Date of Patent: Sep. 20, 2022

(54) FLUIDS FOR IMMERSION COOLING

(71) Applicant: 3M INNOVATIVE PROPERTIES COMPANY, St. Paul, MN (US)

(72) Inventors: Michael J. Bulinski, Stillwater, MN (US); Phillip E. Tuma, Fairbault, MN (US); Michael G. Costello, Afton, MN (US); William M. Lamanna, Stillwater, MN (US); Sean M. Smith, Woodbury, MN (US)

(73) Assignee: 3M INNOVATIVE PROPERTIES COMPANY, St. Paul, MN (US)

( * ) Notice: Subject to any disclaimer, the term of this patent is extended or adjusted under 35 U.S.C. 154(b) by 0 days.

(21) Appl. No.: 16/620,118

(22) PCT Filed: May 24, 2018

(86) PCT No.: PCT/IB2018/053699
§ 371 (c)(1),
(2) Date: Dec. 6, 2019

(87) PCT Pub. No.: WO2018/224908
PCT Pub. Date: Dec. 13, 2018

(65) Prior Publication Data
US 2020/0178414 A1    Jun. 4, 2020

Related U.S. Application Data

(60) Provisional application No. 62/516,413, filed on Jun. 7, 2017.

(51) Int. Cl.
*C09K 5/10* (2006.01)
*H05K 7/20* (2006.01)
(Continued)

(52) U.S. Cl.
CPC ............. *H05K 7/203* (2013.01); *C07C 21/18* (2013.01); *C07C 211/24* (2013.01); *C09K 5/04* (2013.01); *C09K 5/10* (2013.01); *H05K 7/208* (2013.01)

(58) Field of Classification Search
CPC . C09K 5/04; C09K 5/10; H05K 7/203; H05K 7/20236; H05K 7/20936; H05K 7/20927; H05K 7/20763; H05K 7/208
See application file for complete search history.

(56) References Cited

U.S. PATENT DOCUMENTS

| | | | |
|---|---|---|---|
| 4,788,352 | A | 11/1988 | Smutny |
| 7,959,828 | B2 | 6/2011 | Nappa |

(Continued)

FOREIGN PATENT DOCUMENTS

| | | |
|---|---|---|
| WO | WO 2007/053697 | 5/2007 |
| WO | WO 2009-079525 | 6/2009 |

(Continued)

OTHER PUBLICATIONS

Coudures, "Synthese de F-alkyl Oxirannes", Journal of Fluorine Chemistry, Jan. 1984, vol. 24, No. 1, pp. 93-104.

(Continued)

*Primary Examiner* — John R Hardee
(74) *Attorney, Agent, or Firm* — Jeffrey M. Olofson

(57) ABSTRACT

An immersion cooling system includes a housing having an interior space; a heat-generating component disposed within the interior space; and a working fluid liquid disposed within the interior space such that the heat-generating component is in contact with the working fluid liquid. The working fluid comprises a compound having Structural Formula (IA) Each $R_f^1$ and $R_f^2$ is, independently, (i) a linear or branched perhalogenated acyclic alkyl group having 1-6 carbon atoms and optionally contains one or more catenated heteroatoms (Continued)

selected from O or N; or (ii) a perhalogenated 5-7 membered cyclic alkyl group having 3-7 carbon atoms and optionally contains one or more catenated heteroatoms selected from O or N.

15 Claims, 1 Drawing Sheet

(51) Int. Cl.
*C07C 21/18* (2006.01)
*C07C 211/24* (2006.01)
*C09K 5/04* (2006.01)

(56) References Cited

U.S. PATENT DOCUMENTS

| | | | |
|---|---|---|---|
| 8,148,584 B2 | 4/2012 | Hedrick | |
| 10,385,247 B2 | 8/2019 | Kontomaris | |
| 2006/0090881 A1 | 5/2006 | Tuma | |
| 2008/0314073 A1* | 12/2008 | Minor | C09K 5/045 62/498 |
| 2009/0269521 A1* | 10/2009 | Tuma | C23C 26/02 428/32.74 |
| 2011/0315344 A1* | 12/2011 | Campbell | H05K 7/203 165/80.4 |
| 2012/0159976 A1 | 6/2012 | Kontomaris | |
| 2012/0180979 A1 | 7/2012 | Harrington | |
| 2013/0098396 A1 | 4/2013 | Lousenberg | |
| 2013/0160469 A1 | 6/2013 | Kontomaris | |
| 2013/0160478 A1 | 6/2013 | Kontomaris | |
| 2015/0014606 A1 | 1/2015 | Robin | |
| 2016/0044833 A1 | 2/2016 | Krishnan | |
| 2016/0115362 A1 | 4/2016 | Rached | |

FOREIGN PATENT DOCUMENTS

| | | |
|---|---|---|
| WO | WO 2015-095285 | 6/2015 |
| WO | WO 2016-196240 | 12/2016 |

OTHER PUBLICATIONS

Tuma, "Design Considerations Relating to Non-thermal Aspects of Passive 2-Phase Immersion Cooling" Proceedings of 27th Annual IEEE Semiconductor Thermal Measurement and Management Symposium, Mar. 2011, 9 pages.

Tuma, "Fluoroketone C2F5C(O)CF(CF3)2 as a Heat Transfer Fluid for Passive and Pumped 2-Phase Applications" Proceedings of 24th Annual IEEE Semiconductor Thermal Measurement and Management Symposium, Mar. 2008, pp. 174-181.

International Search Report for PCT International Application No. PCT/IB2018/053699, dated Oct. 30, 2018, 4 pages.

Bruice, Paula Yurkanis, Organic Chemistry, 4th edition, pp. 117-118.

Minkin, Vladimir I., Dipole Moments in Organic Chemistry, Dept. of Chemistry, Rostov University, USSR, 1970, Chapter 4.

Borisov, J., Structural Chem., 2002, vol. 43, No. 5, pp. 734-742.

Jatkar, Nature, Feb. 19, 1944, vol. 153, p. 222.

* cited by examiner

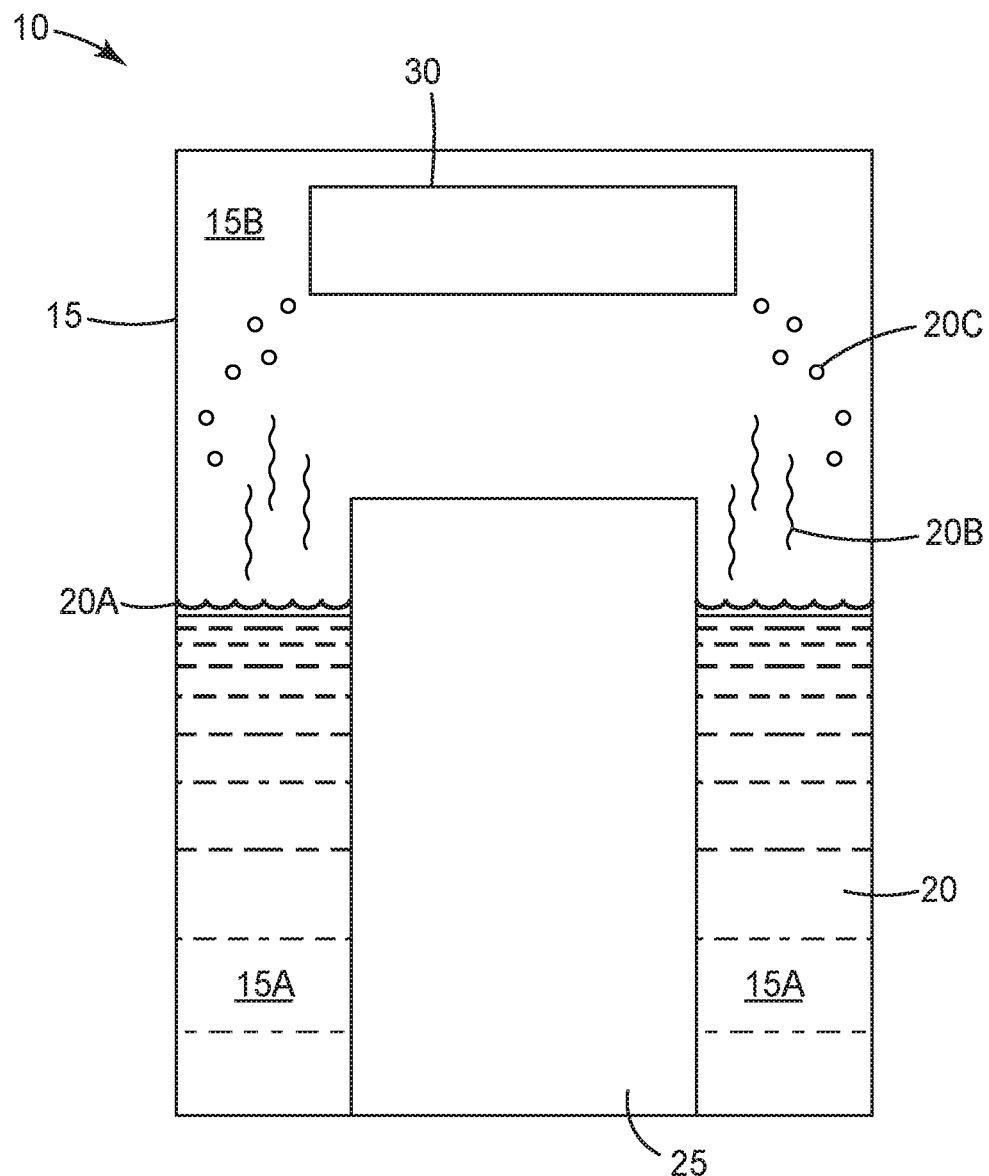

FLUIDS FOR IMMERSION COOLING

CROSS REFERENCE TO RELATED APPLICATIONS

This application is a national stage filing under 35 U.S.C. 371 of PCT/IB2018/053699, filed May 24, 2018, which claims the benefit of U.S. Provisional Application No. 62/516,413, filed Jun. 7, 2017, the disclosure of which is incorporated by reference in its/their entirety herein.

FIELD

The present disclosure relates to compositions useful for immersion cooling systems.

BACKGROUND

Various fluids for use in immersion cooling are described in, for example, P. E. Tuma, "Fluoroketone $C_2F_5C(O)CF(CF_3)_2$ as a Heat Transfer Fluid for Passive and Pumped 2-Phase Applications," 24th IEEE Semi-Therm Symposium, San Jose, Calif., pp. 174-181, Mar. 16-20, 2008; and Tuma, P. E., "Design Considerations Relating to Non-Thermal Aspects of Passive 2-Phase Immersion Cooling," to be published, Proc. 27th IEEE Semi-Therm Symposium, San Jose, Calif., USA, Mar. 20-24, 2011.

SUMMARY

In some embodiments, an immersion cooling system is provided. The immersion cooling system includes a housing having an interior space; a heat-generating component disposed within the interior space; and a working fluid liquid disposed within the interior space such that the heat-generating component is in contact with the working fluid liquid. The working fluid comprises a compound having Structural Formula (IA)

1A

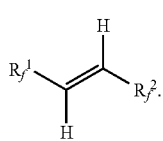

(IA)

Each $R_f^1$ and $R_f^2$ is, independently, (i) a linear or branched perhalogenated acyclic alkyl group having 1-6 carbon atoms and optionally contains one or more catenated heteroatoms selected from O or N; or (ii) a perhalogenated 5-7 membered cyclic alkyl group having 3-7 carbon atoms and optionally contains one or more catenated heteroatoms selected from O or N.

In some embodiments, a method for cooling a heat generating component is provided. The method includes at least partially immersing a heat generating component in a working fluid; and transferring heat from the heat generating component using the working fluid. The working fluid includes a compound having Structural Formula (IA)

1A

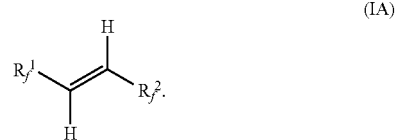

(IA)

Each $R_f^1$ and $R_f^2$ is, independently, (i) a linear or branched perhalogenated acyclic alkyl group having 1-6 carbon atoms and optionally contains one or more catenated heteroatoms selected from O or N; or (ii) a perhalogenated 5-7 membered cyclic alkyl group having 3-7 carbon atoms and optionally contains one or more catenated heteroatoms selected from O or N.

The above summary of the present disclosure is not intended to describe each embodiment of the present disclosure. The details of one or more embodiments of the disclosure are also set forth in the description below. Other features, objects, and advantages of the disclosure will be apparent from the description and from the claims.

DETAILED DESCRIPTION

Large scale computer server systems can perform significant workloads and generate a large amount of heat during their operation. A significant portion of the heat is generated by the operation of these servers. Due in part to the large amount of heat generated, these servers are typically rack mounted and air-cooled via internal fans and/or fans attached to the back of the rack or elsewhere within the server ecosystem. As the need for access to greater and greater processing and storage resources continues to expand, the density of server systems (i.e., the amount of processing power and/or storage placed on a single server, the number of servers placed in a single rack, and/or the number of servers and or racks deployed on a single server farm), continue to increase. With the desire for increasing processing or storage density in these server systems, the thermal challenges that result remain a significant obstacle. Conventional cooling systems (e.g., fan based) require large amounts of power, and the cost of power required to drive such systems increases exponentially with the increase in server densities. Consequently, there exists a need for efficient, low power usage system for cooling the servers, while allowing for the desired increased processing and/or storage densities of the server systems.

Two-phase immersion cooling is an emerging cooling technology for the high-performance server computing market which relies on the heat absorbed in the process of vaporizing a liquid (the cooling fluid) to a gas (i.e., the heat of vaporization). The fluids used in this application must meet certain requirements to be viable in the application. For example, the boiling temperature during operation should be in a range between for example 30° C.-75° C. Generally, this range accommodates maintaining the server components at a sufficiently cool temperature while allowing heat to be dissipated efficiently to an ultimate heat sink (e.g., outside air). The fluid must be inert so that it is compatible with the materials of construction and the electrical components. Certain perfluorinated and partially fluorinated materials may meet this requirement. The fluid should be stable such that it does not react with common contaminants such as water or with reagents such as activated carbon or alumina that might be used to scrub the fluid during operation. The global warming potential (GWP, 100 yr ITH) and ozone depletion potential (ODP) of the parent compound and its degradation products should be below acceptable limits, for example, less than 250 and 0.01, respectively. The fluids should have a dielectric constant (measured at room temperature (about 25° C.) at 1 KHz) of less than 2.5, such that high frequency electronic components and connectors can be submerged in the fluids without significant loss of signal integrity.

Single phase immersion cooling has a long history in computer server cooling. There is no phase change in single phase immersion. Instead the liquid warms and cools as it flows or is pumped to the computer server and a heat exchanger, respectively, thereby transferring heat away from the computer server. The fluids used in single phase immersion cooling of computer servers should meet the same requirements as outlined above with respect to two-phase immersion cooling, except that they typically have higher boiling temperatures exceeding about 40-75° C. to limit evaporative losses.

It is generally understood that perfluorinated liquids may exhibit dielectric constants of 2.0 or less. However, these materials are often associated with high GWP, well outside of the requirement for many industrial applications, including two-phase and single-phase immersion cooling. Therefore, there continues to be a need for working fluids useful for two-phase and single phase immersion cooling that satisfy the dielectric constant requirement of the industry (less than 2.5), while also exhibiting GWPs (100 yr ITH) that are below the acceptable limits for the industry (typically less than about 250).

Generally, the present disclosure is directed to compositions, or working fluids, that exhibit boiling points, reactivity, stability, GWPs, and dielectric constants that render them particularly suitable for use as cooling fluids in two-phase and single phase immersion cooling systems.

As used herein, "catenated heteroatom" means an atom other than carbon (for example, oxygen, nitrogen, or sulfur) that is bonded to at least two carbon atoms in a carbon chain (linear or branched or within a ring) so as to form a carbon-heteroatom-carbon linkage.

As used herein, "fluoro-" (for example, in reference to a group or moiety, such as in the case of "fluoroalkylene" or "fluoroalkyl" or "fluorocarbon") or "fluorinated" means (i) partially fluorinated such that there is at least one carbon-bonded hydrogen atom, or (ii) perfluorinated.

As used herein, "perfluoro-" (for example, in reference to a group or moiety, such as in the case of "perfluoroalkylene" or "perfluoroalkyl" or "perfluorocarbon") or "perfluorinated" means completely fluorinated such that, except as may be otherwise indicated, any carbon-bonded hydrogens are replaced by fluorine atoms.

As used herein, "perhalogenated" means completely halogenated such that, except as may be otherwise indicated, any carbon-bonded hydrogens are replaced by a halogen atom.

As used herein, the singular forms "a", "an", and "the" include plural referents unless the content clearly dictates otherwise. As used in this specification and the appended embodiments, the term "or" is generally employed in its sense including "and/or" unless the content clearly dictates otherwise.

As used herein, the recitation of numerical ranges by endpoints includes all numbers subsumed within that range (e.g. 1 to 5 includes 1, 1.5, 2, 2.75, 3, 3.8, 4, and 5).

Unless otherwise indicated, all numbers expressing quantities or ingredients, measurement of properties and so forth used in the specification and embodiments are to be understood as being modified in all instances by the term "about." Accordingly, unless indicated to the contrary, the numerical parameters set forth in the foregoing specification and attached listing of embodiments can vary depending upon the desired properties sought to be obtained by those skilled in the art utilizing the teachings of the present disclosure. At the very least, and not as an attempt to limit the application of the doctrine of equivalents to the scope of the claimed embodiments, each numerical parameter should at least be construed in light of the number of reported significant digits and by applying ordinary rounding techniques.

In some embodiments, the compositions of the present disclosure may include a composition, or working fluid, that includes a hydrofluoroolefin compound having the following Structural Formula (IA):

1A

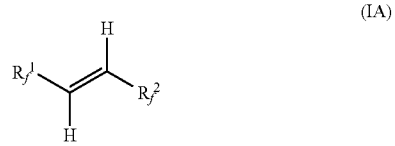

(IA)

Surprisingly, it was discovered that the alkylene segment of Structural Formula (IA), namely an alkylene segment in which each carbon of the segment is bonded to one hydrogen atom and one perhalogenated moiety in the E (or trans) configuration, provides surprisingly low dielectric constants of less than 2.5. No other hydrofluoroolefin structures have been found which provide similarly low dielectric constants. Consequently, it has been discovered that the hydrofluoroolefin compounds of the present disclosure have measured dielectric constants that render them particularly suitable for use as working fluids in immersion cooling systems, particularly those used for the immersion cooling of high performance computer server hardware or devices that operate at high frequencies (e.g. greater than 2 GHz, or greater than 3 GHz, or greater than 4 GHz, or greater than 5 GHz, or greater than 6 GHz, or greater than 7 GHz, or greater than 8 GHz, or greater than 9 GHz, or greater than 10 GHz).

The hydrofluoroolefin compounds of Structural Formula (IA) represent the E (or trans) isomer of a hydrofluoroolefin that can exist in two isomeric forms, the other isomeric form being the Z (or cis) isomer, depicted in Structural Formula (TB):

1B

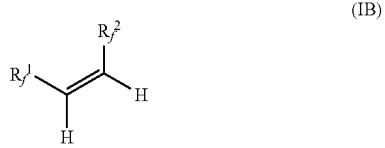

(IB)

Surprisingly, it has also been discovered that the (E) isomer (Structural Formula (IA)) has a significantly lower dielectric constant than its (Z) counterpart and, therefore, compositions rich in the (Z) isomer do not exhibit dielectric constants that would be suitable for use as working fluids in high performance server immersion cooling systems.

In some embodiments, each $R_f^1$ and $R_f^1$ may be, independently, (i) a linear or branched perhalogenated acyclic alkyl group having 1-6, 2-5, or 3-4 carbon atoms and optionally contain one or more catenated heteroatoms selected from O or N; or (ii) a perhalogenated 5-7 membered cyclic alkyl group having 3-7 or 4-6 carbon atoms and optionally containing one or more catenated heteroatoms selected from O or N. In some embodiments, each perhalogenated $R_f^1$ and $R_f^2$ may be substituted with only fluorine atoms or chlorine atoms. In some embodiments, each perhalogenated $R_f^1$ and $R_f^2$ may be substituted with only fluorine atoms and one chlorine atom.

In some embodiments, each $R_f^1$ and $R_f^2$ may be, independently, (i) a linear or branched perfluorinated acyclic alkyl group having 1-6, 2-5, or 3-4 carbon atoms and optionally contain one or more catenated heteroatoms selected from O or N; or (ii) a perfluorinated 5-7 membered cyclic alkyl group having 3-7 or 4-6 carbon atoms and optionally containing one or more catenated heteroatoms selected from O or N. In some embodiments, $R_f^1$ and $R_f^2$ may be the same perfluorinated alkyl groups (acyclic or cyclic, including any catenated heteroatoms).

In some embodiments, the compositions of the present disclosure may be rich in the isomer of Structural Formula (IA) (the E isomer). In this regard, in some embodiments, the compositions of the present disclosure may include hydrofluoroolefins having Structural Formula (IA) in an amount of at least 85, 90, 95, 96, 97, 98, 99, or 99.5 weight percent, based on the total weight of the hydrofluoroolefins having Structural Formula (IA) and (IB) in the composition.

In various embodiments, representative examples of the compounds of general formula (I) include the following:

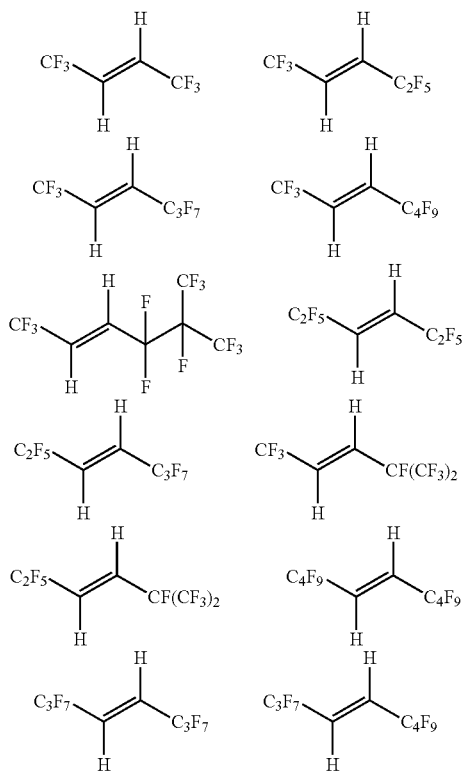

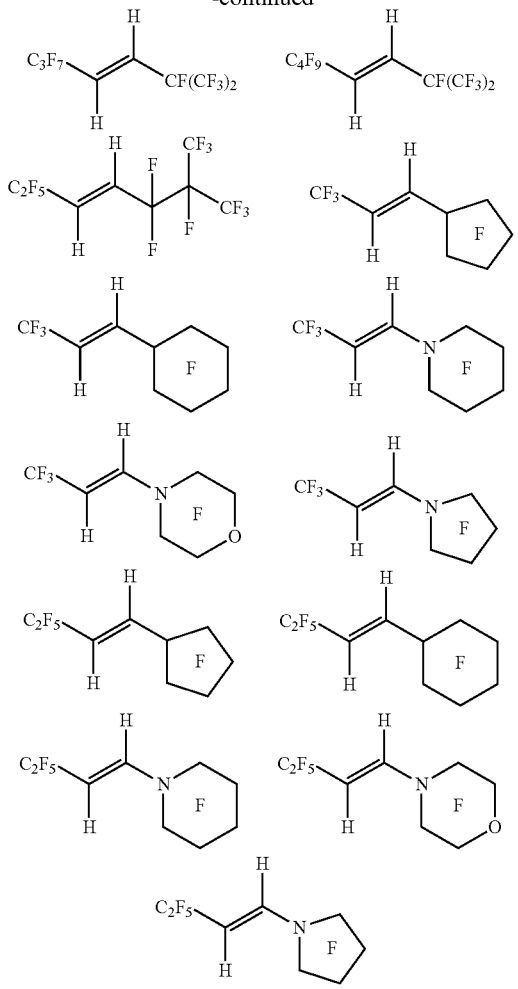

In some embodiments, the hydrofluoroolefin compounds of the present disclosure may be hydrophobic, relatively chemically unreactive, and thermally stable. The hydrofluoroolefin compounds may have a low environmental impact. In this regard, the hydrofluoroolefin compounds of the present disclosure may have a zero, or near zero, ozone depletion potential (ODP) and a global warming potential (GWP, 100 yr ITH) of less than 500, 300, 200, 100 or less than 10. As used herein, GWP is a relative measure of the global warming potential of a compound based on the structure of the compound. The GWP of a compound, as defined by the Intergovernmental Panel on Climate Change (IPCC) in 1990 and updated in 2007, is calculated as the warming due to the release of 1 kilogram of a compound relative to the warming due to the release of 1 kilogram of $CO_2$ over a specified integration time horizon (ITH).

$$GWP_i(t') = \frac{\int_0^{ITH} a_i [C(t)] dt}{\int_0^{ITH} a_{CO_2} [C_{CO_2}(t)] dt} = \frac{\int_0^{ITH} a_i C_{oi} e^{-t/\tau i} dt}{\int_0^{ITH} a_{CO_2} [C_{CO_2}(t)] dt}$$

In this equation $a_i$ is the radiative forcing per unit mass increase of a compound in the atmosphere (the change in the flux of radiation through the atmosphere due to the IR absorbance of that compound), C is the atmospheric concentration of a compound, τ is the atmospheric lifetime of a compound, t is time, and i is the compound of interest. The commonly accepted ITH is 100 years representing a compromise between short-term effects (20 years) and longer-term effects (500 years or longer). The concentration of an organic compound, i, in the atmosphere is assumed to follow pseudo first order kinetics (i.e., exponential decay). The concentration of $CO_2$ over that same time interval incorporates a more complex model for the exchange and removal of $CO_2$ from the atmosphere (the Bern carbon cycle model).

In some embodiments, the fluorine content in the hydrofluoroolefin compounds of the present disclosure may be sufficient to make the compounds non-flammable according to ASTM D-3278-96 e-1 test method ("Flash Point of Liquids by Small Scale Closed Cup Apparatus").

In some embodiments, the hydrofluoroolefin compounds represented by Structural Formula (IA) can be synthesized by the methods described in WO2009079525, WO 2015095285, U.S. Pat. No. 8,148,584, J. Fluorine Chemistry, 24 (1984) 93-104, and WO2016196240.

In some embodiments, the compositions, or working fluids, of the present disclosure may include at least 25%, at least 50%, at least 70%, at least 80%, at least 90%, at least 95%, or at least 99% by weight of the above-described hydrofluoroolefins, based on the total weight of the composition. In addition to the hydrofluoroolefins, the compositions may include a total of up to 75%, up to 50%, up to 30%, up to 20%, up to 10%, up to 5%, or up to 1% by weight of one or more of the following components (individually or in any combination): ethers, alkanes, perfluoroalkenes, alkenes, haloalkenes, perfluorocarbons, perfluorinated tertiary amines, perfluoroethers, cycloalkanes, esters, perfluoroketones, ketones, oxiranes, aromatics, siloxanes, hydrochlorocarbons, hydrochlorofluorocarbons, hydrofluorocarbons, hydrofluoroolefins, hydrochloroolefins, hydrochlorofluoroolefins, hydrofluoroethers, or mixtures thereof based on the total weight of the working fluid; or alkanes, perfluoroalkenes, haloalkenes, perfluorocarbons, perfluorinated tertiary amines, perfluoroethers, cycloalkanes, perfluoroketones, aromatics, siloxanes, hydrochlorocarbons, hydrochlorofluorocarbons, hydrofluorocarbons, hydrofluoroolefins, hydrochlorofluoroolefins, hydrofluoroethers, or mixtures thereof, based on the total weight of the working fluid. Such additional components can be chosen to modify or enhance the properties of a composition for a particular use.

In some embodiments, the compositions, or working fluids of the present disclosure may have dielectric constants that are less than 2.5, less than 2.4, less than 2.3, less than 2.2, less than 2.1, less than 2.0, or less than 1.9, as measured in accordance with ASTM D150 at room temperature.

In some embodiments, the compositions or working fluids of the present disclosure may have a boiling point between 30-75° C., or 35-75° C., 40-75° C., or 45-75° C. In some embodiments, the compositions or working fluids of the present invention may have a boiling point greater than 40° C., or greater than 50° C., or greater than 60° C., greater than 70° C., or greater than 75° C.

In some embodiments, the present disclosure may be directed to an immersion cooling system that includes the above-discussed hydrofluoroolefin-containing working fluids. The immersion cooling systems may be single-phase or two-phase immersion cooling systems.

In some embodiments, the immersion cooling systems may operate as two-phase vaporization-condensation cooling systems for cooling one or more heat generating components. As shown in FIG. 1, in some embodiments, a two-phase immersion cooling system 10 may include a housing 10 having an interior space 15. Within a lower volume 15A of interior space 15, a liquid phase 20 of a hydrofluoroolefin-containing working fluid having an upper liquid surface 20A (i.e., the topmost level of the liquid phase 20) may be disposed. The interior space 15 may also include an upper volume 15B extending from the liquid surface 20A up to an upper portion 10A of the housing 10.

In some embodiments, a heat generating component 25 may be disposed within the interior space 15 such that it is at least partially immersed (and up to fully immersed) in the liquid phase 20 of the working fluid. That is, while heat generating component 25 is illustrated as being only partially submerged below the upper liquid surface 20A, in some embodiments, the heat generating component 25 may be fully submerged below the liquid surface 20A. In some embodiments, the heat generating components may include one or more electronic devices, such as computing servers.

In various embodiments, a heat exchanger 30 (e.g., a condenser) may be disposed within the upper volume 15B. Generally, the heat exchanger 30 may be configured such that it is able to condense a vapor phase 20B of the working fluid that is generated as a result of the heat that is produced by the heat generating element 25. For example, the heat exchanger 30 may have an external surface that is maintained at a temperature that is lower than the condensation temperature of a vapor phase of the working fluid. In this regard, at the heat exchanger 30, a rising vapor phase 20B of the working fluid may be condensed back to liquid phase or condensate 20C by releasing latent heat to the heat exchanger 30 as the rising vapor phase 20B comes into contact with the heat exchanger 30. The resulting condensate 20C may then be returned back to the liquid phase 20 disposed in the lower volume of 15A.

In some embodiments, the present disclosure may be directed to an immersion cooling system which operates by single phase immersion cooling. Generally, the single phase immersion cooling system is similar to that of the two phase system in that it may include a heat generating component disposed within the interior space of a housing such that it is at least partially immersed (and up to fully immersed) in the liquid phase of the working fluid. The single phase system may further include a pump and a heat exchanger, the pump operating to move the working fluid to and from the heat generating components and the heat exchanger, and the heat exchanger operating to cool the working fluid. The heat exchanger may be disposed within or external to the housing.

While the present disclosure describes examples of suitable two-phase and single-phase immersion cooling systems, it is to be appreciated that the benefits and advantages of the hydrofluoroolefin-containing working fluids of the present disclosure may be realized in any known two-phase or single phase immersion cooling system.

In some embodiments, the present disclosure may be directed to methods for cooling electronic components. Generally, the methods may include at least partially immersing a heat generating component (e.g., a computer server) in a liquid that includes the above-described hydroolefin compound or working fluid. The method may further include transferring heat from the heat generating component using the above-described hydroolefin compound or working fluid.

Listing of Embodiments

1. An immersion cooling system comprising:
   a housing having an interior space;
   a heat-generating component disposed within the interior space;
   a working fluid liquid within the interior space positioned such that the heat-generating component is in contact with the working fluid liquid;
   wherein the working fluid comprises a compound having Structural Formula (IA)

1A

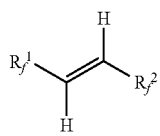

(IA)

wherein each $R_f^1$ and $R_f^2$ is, independently, (i) a linear or branched perhalogenated acyclic alkyl group having 1-6 carbon atoms and optionally contains one or more catenated heteroatoms selected from O or N; or (ii) a perhalogenated 5-7 membered cyclic alkyl group having 3-7 carbon atoms and optionally contains one or more catenated heteroatoms selected from O or N.
2. The immersion cooling system of embodiment 1, wherein each $R_f^1$ and $R_f^2$ is, independently, (i) a linear or branched perfluorinated acyclic alkyl group having 1-6 carbon atoms and optionally contains one or more catenated heteroatoms selected from O or N; or (ii) a perfluorinated 5-7 membered cyclic alkyl group having 3-7 carbon atoms and optionally contains one or more catenated heteroatoms selected from O or N.
3. The immersion cooling system of embodiment 2, wherein $R_f^1$ and $R_f^2$ are the same perfluorinated alkyl group.
4. The immersion cooling system of any one of embodiments 1-3, wherein the compound having Structural Formula (IA) is present in the working fluid in an amount of at least 90 percent by weight based on the total weight of the compound having Structural Formula (IA) and a compound having Structural Formula (IB)

1B

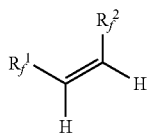

(IB)

in the working fluid.
5. The immersion cooling system of any one of embodiments 1-4, wherein the compound having Structural Formula (IA) is present in the working fluid in an amount of at least 50 percent by weight based on the total weight of the working fluid.
6. The immersion cooling system of any one of embodiments 1-5, wherein the working fluid has a dielectric constant less than 2.5.
7. The immersion cooling system of any one of embodiments 1-6, wherein the working fluid has a boiling point of 30-75° C.
8. The immersion cooling system of any one of embodiments 1-7, wherein the working fluid has a boiling point of greater than 75° C.
9. The immersion cooling system of any one of embodiments 1-8, wherein the heat-generating component comprises an electronic device.
10. The immersion cooling system of embodiment 9, wherein the electronic device comprises a computing server.
11. The immersion cooling system of embodiment 10, wherein the computing server operates at frequency of greater than 3 GHz.
12. The immersion cooling system of any one of embodiments 1-11, wherein the immersion cooling system further comprises a heat exchanger disposed within the system such that upon vaporization of the working fluid liquid, the working fluid vapor contacts the heat exchanger;
13. The immersion cooling system of any one of embodiments 1-12, wherein the immersion cooling system comprises a two-phase immersion cooling system.
14. The immersion cooling system of any one of embodiments 1-11, wherein the immersion cooling system comprises a single-phase immersion cooling system.
15. The immersion cooling system of any one of embodiments 1-11 or 14, wherein the immersion cooling system further comprises a pump that is configured to move the working fluid to and from a heat exchanger.

The operation of the present disclosure will be further described with regard to the following detailed examples. These examples are offered to further illustrate various embodiments and techniques. It should be understood, however, that many variations and modifications may be made while remaining within the scope of the present disclosure.

EXAMPLES

The present disclosure is more particularly described in the following examples that are intended as illustrations only, since numerous modifications and variations within the scope of the present disclosure will be apparent to those skilled in the art. Unless otherwise noted, all parts, percentages, and ratios reported in the following examples are on a weight basis. Reagents were purchased from Sigma Aldrich Company, St. Louis, Mo., USA, unless otherwise indicated.

Examples 1, 3, and 4, and Comparative Examples CE2, CE3, and CE4 were purchased from Synquest Laboratories, Alachua Fla., USA, and used as received.

To prepare Example 2, antimony pentafluoride (30 g, 138.41 mmol) was charged in a 600 mL Parr reactor. The reactor was sealed and cooled in dry ice. Vacuum was then applied when the reactor was cold. Then 1,1-difluoro-N-(trifluoromethyl)methanimine (205 g, 1541.1 mmol, prepared by the decarboxylation of bis(trifluoromethyl)carbamic fluoride, which can be prepared by the electrochemical fluorination of dimethyl formamide) and (E)-1,3,3,3-tetrafluoroprop-1-ene (240 g, 2104.5 mmol, available from Honeywell) were then charged sequentially to the headspace of the reactor as liquids. The reactor was then placed in the stand, stirred and allowed to warm to room temperature. Once at room temperature, the heat on the reactor was gradually increased to 70° C. After holding for 16 hours the reactor was cooled, vented and poured over ice. The weight of crude fluorochemical product that was recovered was 138. g. Approximately 68% of the total mass recovered is the desired product according to GC analysis. The material was subsequently purified by fractional distillation and the structure was verified to be primarily the (E)

isomer of 3,3,3-trifluoro-N,N-bis(trifluoromethyl)prop-1-en-1-amine by GC/MS and F19 and H1 NMR.

To prepare Comparative Example CE1, in a 1 L 3-neck round bottom flask equipped with overhead stirring, thermocouple, cold water condenser, dry N2 line and an addition funnel, sodium borohydride (5.23 g, 138 mmol) and diethylene glycol dimethyl ether (102 g) were charged. The mixture was stirred to dissolve some of the borohydride. The mixture was then cooled down to −72° C., 1,1,1,3,4,4,5,5,5-nonafluoro-2-(trifluoromethyl)pent-2-ene (103 g, 343.285 mmol) was then added via addition funnel dropwise with stirring while maintaining the temperature between −72° C. to −63° C. Once the addition was complete, the batch was stirred at −72° C. for another hour. Then reaction mixture was warmed to 15° C., and quenched with 10 g water and 400 g 35% H3PO4. The reaction mixture was transferred to a separatory funnel, 90 g product was collected. GC-MS results indicate the crude product consisted of monohydride and dihydride mainly. The desired monohydride was further purified by fractional distillation yielding the pure material. The boiling point of the material is 52° C. The structure was confirmed by GC/MS and F19 and H1 NMR.

Dielectric constants were determined using ASTM D150 at room temperature with the average value reported at 1 KHz.

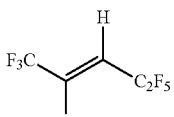

| Example | Chemical Structure | Chemical Name | Boiling point (° C., at 760 mm Hg) | Dielectric Constant at 1 kHz | % (E/Z) |
|---|---|---|---|---|---|
| 1 | 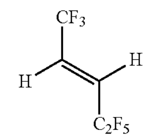 | (E)-1,1,1,4,4,5,5,5-octafluoropent-2-ene | 33 | 2.1 | 96%(E) 4%(Z) |
| 2 | 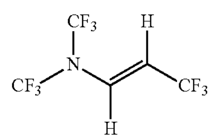 [SMILES: FC(F)(F)/C=C/N(C(F)(F)F)C(F)(F)F] | (E)-3,3,3-trifluoro-N,N-bis(trifluoromethyl)prop-1-en-1-amine | 48 | 2.3 | 94%(E) 6%(Z) |
| 3 | 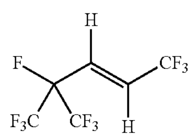 | (E)-1,1,1,4,5,5,5-heptafluoro-4-(trifluoromethyl)pent-2-ene | 50 | 1.85 | 98%(E) 2% (Z) |
| 4 | 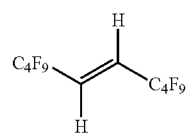 | (E)-1,1,1,2,2,3,3,4,4,7,7,8,8,9,9,10,10,10-octadecafluorodec-5-ene | ~140 | 1.93 | 98%(E) 2% (Z) |

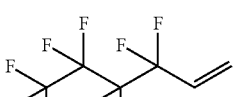

| Comparative Example | Chemical Structure | Chemical Name | Boiling point (° C., at 760 mm Hg) | Dielectric Constant at 1 kHz |
|---|---|---|---|---|
| CE1 | 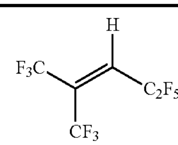 | 1,1,1,4,4,5,5,5-octafluoro-2-(trifluoromethyl)pent-2-ene | 52 | 3.0 |
| CE2 | 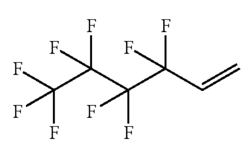 | 3,3,4,4,5,5,6,6,6-nonafluorohex-1-ene | 59 | 5.8 |
| CE3 | 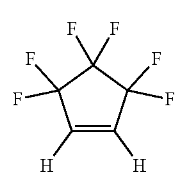 [SMILES: FC1(F)C=CC(F)(F)C1(F)F] | (Z)-3,3,4,4,5,5-hexafluorocyclopent-1-ene | 72 | 20 |

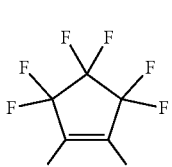

-continued

| Comparative Example | Chemical Structure | Chemical Name | Boiling point (° C., at 760 mm Hg) | Dielectric Constant at 1 kHz |
|---|---|---|---|---|
| CE4 | 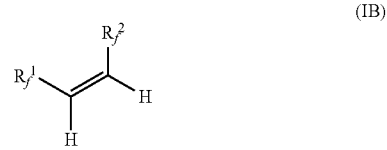 | (Z)-1,1,1,4,4,4-hexafluorobut-2-ene | 33 | 16.6 |

Although specific embodiments have been illustrated and described herein for purposes of description of some embodiments, it will be appreciated by those of ordinary skill in the art that a wide variety of alternate and/or equivalent implementations may be substituted for the specific embodiments shown and described without departing from the scope of the present disclosure.

What is claimed is:

1. An immersion cooling system comprising:
a housing having an interior space;
a heat-generating component disposed within the interior space; and
a working fluid liquid disposed within the interior space such that the heat-generating component is in contact with the working fluid liquid;
wherein the working fluid comprises a compound having Structural Formula (IA)

1A

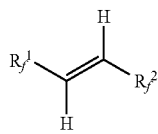

(IA)

wherein each $R_f^1$ and $R_f^2$ is, independently, (i) a linear or branched perhalogenated acyclic alkyl group having 1-6 carbon atoms and optionally contains one or more catenated heteroatoms selected from 0 or N; or (ii) a perhalogenated 5-7 membered cyclic alkyl group having 3-7 carbon atoms and optionally contains one or more catenated heteroatoms selected from O or N; and
wherein the working fluid has a dielectric constant less than 2.5.

2. The immersion cooling system of claim 1, wherein each $R_f^1$ and $R_f^2$ is, independently, (i) a linear or branched perfluorinated acyclic alkyl group having 1-6 carbon atoms and optionally contains one or more catenated heteroatoms selected from O or N; or (ii) a perfluorinated 5-7 membered cyclic alkyl group having 3-7 carbon atoms and optionally contains one or more catenated heteroatoms selected from O or N.

3. The immersion cooling system of claim 2, wherein $R_f^1$ and $R_f^2$ are the same perfluorinated alkyl group.

4. The immersion cooling system of claim 1, wherein the compound having Structural Formula (IA) is present in the working fluid in an amount of at least 90 percent by weight based on the total weight of the compound having Structural Formula (IA) and a compound having Structural Formula (IB)

1B (IB)

[structure showing $R_f^1$, $R_f^2$, H, H on a double bond]

in the working fluid.

5. The immersion cooling system of claim 1, wherein the compound having Structural Formula (IA) is present in the working fluid in an amount of at least 50 percent by weight based on the total weight of the working fluid.

6. The immersion cooling system of claim 1, wherein the working fluid has a boiling point of 30-75° C.

7. The immersion cooling system of claim 1, wherein the working fluid has a boiling point of greater than 75° C.

8. The immersion cooling system of claim 1, wherein the heat-generating component comprises an electronic device.

9. The immersion cooling system of claim 8, wherein the electronic device comprises a computing server.

10. The immersion cooling system of claim 9, wherein the computing server operates at frequency of greater than 3 GHz.

11. The immersion cooling system of claim 1, wherein the immersion cooling system further comprises a heat exchanger disposed within the system such that upon vaporization of the working fluid liquid, the working fluid vapor contacts the heat exchanger.

12. The immersion cooling system of claim 1, wherein the immersion cooling system comprises a two-phase immersion cooling system.

13. The immersion cooling system of claim 1, wherein the immersion cooling system comprises a single-phase immersion cooling system.

14. The immersion cooling system of claim 1, wherein the immersion cooling system further comprises a pump that is configured to move the working fluid to and from a heat exchanger.

15. A method for cooling a heat generating component, the method comprising:
at least partially immersing a heat generating component in a working fluid; and
transferring heat from the heat generating component using the working fluid;

wherein the working fluid comprises a compound having Structural Formula (IA)

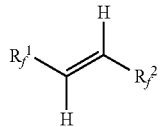

(IA)

wherein each $R_f^1$ and $R_f^2$ is, independently, (i) a linear or branched perhalogenated acyclic alkyl group having 1-6 carbon atoms and optionally contains one or more catenated heteroatoms selected from O or N; or (ii) a perhalogenated 5-7 membered cyclic alkyl group having 3-7 carbon atoms and optionally contains one or more catenated heteroatoms selected from O or N; and wherein the working fluid has a dielectric constant less than 2.5.

* * * * *